United States Patent
Ingman et al.

(10) Patent No.: US 9,655,823 B2
(45) Date of Patent: May 23, 2017

(54) COSMETIC COMPOSITION

(71) Applicant: LEOREX LTD., Haifa (IL)

(72) Inventors: Dov Ingman, Herzliya (IL); Erez Manor, Herzlia (IL)

(73) Assignee: LEOREX LTD., Haifa (IL)

( * ) Notice: Subject to any disclaimer, the term of this patent is extended or adjusted under 35 U.S.C. 154(b) by 0 days.

(21) Appl. No.: 14/780,540

(22) PCT Filed: Apr. 25, 2014

(86) PCT No.: PCT/IB2014/061014
§ 371 (c)(1),
(2) Date: Sep. 27, 2015

(87) PCT Pub. No.: WO2014/174495
PCT Pub. Date: Oct. 30, 2014

(65) Prior Publication Data
US 2016/0045409 A1    Feb. 18, 2016

(30) Foreign Application Priority Data

Apr. 25, 2013 (IL) .......................... 225985

(51) Int. Cl.
| *A61K 8/02* | (2006.01) |
| *A61K 8/25* | (2006.01) |
| *A61Q 19/00* | (2006.01) |
| *A61Q 19/08* | (2006.01) |
| *A61K 8/04* | (2006.01) |
| *A61K 8/19* | (2006.01) |
| *A61K 8/84* | (2006.01) |
| *A61K 8/88* | (2006.01) |
| *A61K 8/92* | (2006.01) |

(52) U.S. Cl.
CPC .............. *A61K 8/25* (2013.01); *A61K 8/0241* (2013.01); *A61K 8/0245* (2013.01); *A61K 8/044* (2013.01); *A61K 8/046* (2013.01); *A61K 8/19* (2013.01); *A61K 8/84* (2013.01); *A61K 8/88* (2013.01); *A61K 8/92* (2013.01); *A61Q 19/00* (2013.01); *A61Q 19/08* (2013.01); *A61K 2800/412* (2013.01); *A61K 2800/413* (2013.01); *A61K 2800/52* (2013.01); *A61K 2800/548* (2013.01)

(58) Field of Classification Search
None
See application file for complete search history.

(56) References Cited

U.S. PATENT DOCUMENTS

| 4,664,909 A | * | 5/1987 | Marschner | A61K 8/19 424/59 |
|---|---|---|---|---|
| 6,620,407 B1 | | 9/2003 | Gers-Barlag et al. | |
| 2003/0129151 A1 | * | 7/2003 | Candau | A61Q 17/04 424/59 |
| 2004/0127579 A1 | * | 7/2004 | Lannibois-Drean | B01J 13/00 516/21 |
| 2006/0257437 A1 | * | 11/2006 | Ingman | A61K 8/19 424/401 |
| 2010/0266649 A1 | | 10/2010 | Maitra et al. | |

OTHER PUBLICATIONS

Ingman et al. (WO 03/049706).*

* cited by examiner

*Primary Examiner* — Robert A Wax
*Assistant Examiner* — Quanglong Truong
(74) *Attorney, Agent, or Firm* — Marc Van Dyke; Fourth Dimension IP

(57) ABSTRACT

A topically administrable composition comprises an aqueous suspension (e.g. a quick-drying aqueous solution), said aqueous suspension having disposed there within amphiphilic micro-particles having diameters in the range of 1-100 µm, wherein said aqueous suspension comprises: A. hydrophobic nanoparticles of modified metal oxide and/or modified silicon oxide having diameters in the range of 1-150 nm; B. hydrophilic nanoparticles of metal oxide and/or silicon oxide having diameters in the range of 1-150 nm; and C. gas bubbles which are bounded by an internal layer of said hydrophobic nanoparticles and an external layer of said hydrophilic nanoparticles. In some embodiments, the gas-bubbles are air-bubbles.

21 Claims, No Drawings

COSMETIC COMPOSITION

FIELD OF THE INVENTION

The invention relates to cosmetic composition and in particular to a cosmetic composition for using in improvement the appearance of skin and reducing skin wrinkles.

BACKGROUND OF THE INVENTION

Numerous cosmetics exist for treatment and concealment of wrinkles. The problem of how to alleviate wrinkling and improve the health and appearance of wrinkled skin is ubiquitous and cosmetic methods for treatment of wrinkles are avidly sought.

In previous publication WO 03049706 (WO '706) one of the inventors of describes an aqueous liquid or emulsion comprising: water; hydrophilic particles consisting of oxide particles having surfaces covered with polar radicals; and hydrophobic particles; wherein the hydrophilic and hydrophobic particles form shells encapsulating a gas that are suspended in the water, said shells comprising an external layer of hydrophilic particles and an internal layer of hydrophobic particles adjacent to the layer of hydrophilic particles. The WO '706 further describes a powder comprising: water; hydrophilic oxide particles; and hydrophobic oxide particles; wherein the water is encapsulated in shells comprising an external layer of hydrophobic oxide particles and an internal layer of hydrophilic oxide particles adjacent to the layer of hydrophobic oxide particles. There are no amphiphilic particles in this aqueous liquid or emulsion composition.

WO '706 specifically refers to diameters of hydrophilic and hydrophobic nano-particles that range from about 5 nm to about 150 nm (page 9, lines 1-2). It further indicates that hydrophilic particles and hydrophobic particles preferably have a specific surface (i.e. surface to mass ratio) that is greater than about 100 $m^2/g$ and preferably substantially greater. It is advantageous for hydrophilic and hydrophobic particles to be as small as possible and to the extent that the specific surface of a particle is greater, the size of the particle is smaller (page 9, lines 12-16).

US 20060257437 of one of the inventors of present invention relates to a topical cosmetic composition which comprises water, hydrophobic nano-particles (preferably hydrophobic silica), and hydrophilic nano-particles (preferably hydrophilic silica), and a soluble electrolyte, capable of releasing free ions in an aqueous environment. In the presence of hydrophilic and hydrophobic nano-particles, the composition simultaneously comprises bounded shells encapsulating a gaseous material, dispersed in water and bounded shells encapsulating aqueous solution droplets. More specifically, the bounded shells encapsulating gas are coated by an external layer of hydrophilic nano-particles and an internal layer of hydrophobic nano-particles and the bounded shells encapsulating aqueous solution droplets are coated by an external layer of hydrophobic nano-particles and an internal layer of hydrophilic nano-particles. There are no amphiphilic particles in this composition.

The inventors of present invention further relate in IL 192201 to a two-phase skin-care composition, which simultaneously comprises separate, immiscible, stable hypotonic and hypertonic phases, relatively to the skin, wherein at least one phase consists of a plurality of separate, immiscible, stable hypertonic or hypotonic entities. Applying said composition onto the skin resulted in multidirectional movement of ions from multiple, individual hypertonic entities into the skin, yielding a heterogeneous electrical field in the treated skin area with a substantial higher potential gradient, side by side with multidirectional flow of fluid, containing water and optionally skin-care ingredients, from the multiple, individual hypotonic entities towards hypertonic ones and the skin. The separate, immiscible, stable hypotonic and/or hypertonic entities are bounded water (or aqueous suspension) droplets having internal layer(s) of hydrophilic nano-particles and external layer(s) of hydrophobic nano-particles. There are no amphiphilic particles in this two-phase composition.

The brochure by Arkema ("Orgasol—New Senses for Skin Care") and U.S. Pat. No. 8,287,950 describe the skin care product Orgasol® Caresse which comprises round shaped uniformed amphiphilic polyamide or copolyesteramide micro-particles having average particle size of 10 μm (specific surface area: about 8 $m^2/g$). During the production of said amphiphilic micro-particles, Aerosil® R 972 (hydrophobic fumed silica with a pH of between 3.6 and 4.4, composed of individual primary particles with a diameter of 16 nm, which have a tendency to agglomerate into larger particles, and with a specific surface of 110 $m^2/g$ (ISO 5794-1)). This silica which was subjected to a hydrophobic treatment using dimethylsilyl or trimethylsilyl groups, was used as a filler. After filtering off and drying, a polyamide-12 powder is obtained which is composed of spheroidal particles. These amphiphilic micro-particles having hydrophilic-hydrophobic balance that makes their dispersion easy in oil/water emulsions.

None of WO '706, US 20060257437 and IL 192201 refer to an aqueous suspension or emulsion that comprises said combination of air, individual hydrophobic and hydrophilic metal (and/or silicon) oxide nano-particles, and at least one type of amphiphilic micro-particles having diameters in the range of 1-100 μm.

SUMMARY OF THE INVENTION

Embodiments of the present invention relate to the surprising discovery that addition of amphiphilic particles (e.g. Orgasol Caresse) to certain cosmetic quick-drying aqueous suspensions transforms the suspension into a composition that is not quick drying, thereby extending the shelf-life and stability under heat.

PCT/IL2002/000891 of one of the present inventors describes a wrinkle cream comprising hydrophilic and hydrophobic particles. In contrast to every wrinkle cream of which the present inventors are aware (which are typically oily), the composition of PCT/IL2002/000891 are quick-drying, to an extent which precludes normal usage in a conventional cosmetics jar.

During typical use, the jar would be opened several times a week (each time from several seconds to a few minutes). For a normal non-'quick-drying' composition, it would be expected that a jar containing 30-50 ml would last for at least 4 weeks and preferably at least 8. The present inventors have observed that the composition of PCT/IL2002/000891, under normal conditionals, typically lasts for at most about 2 weeks, due to its 'quick drying nature.' In contrast to conventional non-quick-drying compositions, which have a shelf life of at least a year when in a sealed jar, the quick-drying composition of PCT/IL2002/000891 has a shelf-life of at most a few months. Furthermore, the quick-drying composition loses structural stability when exposed to prolonged (a day or longer) of heat over 40 degrees Celsius, as may happen during shipment or storage in hot warehouses. Many commercial wrinkle creams do not deteriorate under similar conditions.

Not wishing to be bound by theory, it is postulated that a presence of the amphiphilic particles within the composition may form clusters of bubbles, increasing the 'stability' of the composition against water evaporation and its structural stability and storage in warm temperatures.

Thus, it was surprisingly found that addition of amphiphilic particles, having diameters in the range of 1-100 μm (hereinafter referred to as "micro-amphiphilic particles" or "amphiphilic micro-particles") to the compositions described in WO '706, US 20060257437 and IL 192201, resulted in production of a higher stable and reliable cosmetic composition, having longer shelf-life and effective reproducible results in displaying a substantial improvement in concealing wrinkles and in treating disorders leading to damage to skin appearance. It is speculated that the role of the amphiphilic-micro-particles in such composition is inter alia to increase the attraction to hydrophobic and hydrophilic groups (including water molecules) at the composition surface, resulted in stabilizing the composition and reducing the undesired loss of water by evaporation. Thus, it seems that the presence of such amphiphilic particles substantially reduces the amount of evaporated water and consequently yields a composition having higher stability and longer shelf-life. Also, the presence of amphiphilic micro-particles which carries on their surface zones of hydrophilic groups attracts the water molecules and consequently reduces the undesired evaporation of water from the composition. Hence, the amphiphilic micro-particles are very useful in formulating a rather stable cosmetic composition, having substantially longer shelf-life, for concealing wrinkles and for treating and/or improving other disorders to the skin appearance. In addition, the presence of amphiphilic or micro-particles in the composition of present invention enhances and accelerates the function of the composition as a result of firmly contact and attachment of the composition to both hydrophobic regions of the skin (such as, sebum) and hydrophilic regions (such as, sweat glands), as well as regions which represent a mixture of hydrophobic/philic characters.

The present invention overcomes the shortcomings of the cosmetic compositions described in WO '706, US 20060257437 and IL 192201. More particularly, in addition to presence of hydrophobic metal (including silicon) oxide nano-particles and hydrophilic metal (including silicon) oxide nano-particles, the cosmetic composition of present invention comprises an amount of amphiphilic micro-particles, that serve in improving the stability and activity of the composition, as well as increasing its shelf-life. Thus, the aqueous suspension (or the emulsion) of present invention comprises a new particular combination of water, air, hydrophobic metal (including silicon) oxide nano-particles, hydrophilic metal (including silicon) nano-particles and amphiphilic micro-particles.

It is now disclosed a topically administrable composition comprising: an aqueous suspension, said aqueous suspension having disposed therewithin amphiphilic micro-particles having diameters in the range of 1-100 μm, wherein said aqueous suspension comprises: A. hydrophobic nanoparticles of modified metal oxide and/or modified silicon oxide having diameters in the range of 1-150 nm; B. hydrophilic nanoparticles of metal oxide and/or silicon oxide having diameters in the range of 1-150 nm; and C. gas bubbles which are bounded by an internal layer of said hydrophobic nanoparticles and an external layer of said hydrophilic nanoparticles.

In some embodiments, the aqueous suspension is quick-drying.

In some embodiments, the gas is air.

In some embodiments, the hydrophobic nanoparticles of modified metal oxide and/or modified silicon oxide have diameters in the range of 1-75 nm, or 1-50 nm, or 1-25 nm, or 1-15 nm, or 1-10 nm.

In some embodiments, the hydrophilic nanoparticles of metal oxide and/or silicon oxide have diameters in the range of 1-75 nm, or 1-50 nm, or 1-25 nm, or 1-15 nm, or 1-10 nm.

In some embodiments, the amphiphilic micro-particles have diameters in the range of 1-50 μm, or in the range of 1-25 μm, or in the range of 1-15 μm, or in the range of 1-10 μm.

In some embodiments, (i) the amphiphilic particles are present in the composition in an amount of a–b % by weight; (ii) a and b are both positive numbers; (iii) a value of a is at least 1 or at least 2 or at least 3 or at least 4 or at least 5 and/or a value of b is at most 20 or at most 15 or at most 10 or at most 8 or at most 6 or at most 5 or at most 4.

In some embodiments, the amphiphilic micro-particles are spherical.

In some embodiments, the amphiphilic micro-particles comprise a plastic and/or comprise a polyamine and/or comprise a copolyesteramide.

In some embodiments, the amphiphilic micro-particles have a microporosity so that a per-particle surface area is between 1 and 100 meters2/gram.

In some embodiments, said hydrophobic modified metal oxide nano-particles are present in an amount of 1-3.5% by weight of said composition; said metal oxide nano-particles are present in an amount of 3-14% by weight of said composition; said amphiphilic particles are present in an amount of 2-4% by weight; of said composition; and the mass ratio of hydrophilic particles to hydrophobic particles is in the range of 3:1 to 6:1.

In some embodiments, said hydrophobic modified nano-particles metal oxide and/or silicon oxide are present in said composition in an amount of 3-14% by weight; (ii) hydrophilic nano-particles of metal oxide and/or silicon oxide in an amount of 1-3.5% by weight; (iii) amphiphilic particles in an amount of 2-4% by weight; wherein the ratio hydrophilic/hydrophobic mass is in the range of 1:3 to 1:6 by weight.

In some embodiments, the composition comprises at least one of mineral salts, vitamins, oils, flavonoids and pigments.

In some embodiments, the composition is in any one of the following forms: cream or cream-like, lotion, paste, ointment, gel and foam.

In some embodiments, the composition is osmotic monotonic relative to human skin.

In some embodiments, the composition is hypotonic relative to human skin.

In some embodiments, the composition is hypertonic relative to human skin.

In some embodiments, the composition is isotonic relative to the treated skin.

In some embodiments, the composition is simultaneously an osmotic multi-tonic relative to the treated skin.

In some embodiments, the composition is simultaneously hypotonic and hypertonic relative to the treated skin.

In some embodiments, the composition is for use in cosmetic applications.

In some embodiments, the composition is comprising an aqueous suspension which comprises:

(i) hydrophobic metal, including silicon, oxide nano-particles, having diameters in the range of 1-150 nm and at least 90% of entire particles' surface displays hydrophobic character;
(ii) hydrophilic metal, including silicon, oxide nano-particles, having diameters in the range of 1-150 nm and at least 90% of entire particles' surface displays hydrophilic character;
(iii) amphiphilic particles having diameters in the range of 1-100 μm, wherein 20-80% of entire particles' surface displays hydrophobic character and the rest of particles surface displays hydrophilic character.

In some embodiments, the amphiphilic particles are nano-particles having diameters in the range of 1-150 nm.

In some embodiments, the amphiphilic particles are micro-particles having diameters in the range of 1-100 μm.

In some embodiments, the amphiphilic particles are nano-particles, having diameters in the range of 1-150 nm and micro-particles, having diameters in the range of 1-100 μm.

In some embodiments, the composition comprises air bubbles bounded by internal layer(s) consisting of hydrophobic nano-particles and external layer(s) consisting of hydrophilic nano-particles.

In some embodiments, the composition comprises:
(i) hydrophobic nano-particles in an amount of 1-3.5% (by weight);
(ii) hydrophilic nano-particles in an amount of 3-14% (by weight);
(iii) amphiphilic particles in an amount of 2-4% (by weight);
wherein the ratio hydrophilic/hydrophobic mass should be in the range of 3:1 to 6:1 (by weight).

In some embodiments, the composition further comprises oil.

In some embodiments, the composition, which comprises water (or aqueous suspension) droplets bounded by internal layer(s) consisting of hydrophilic nano-particles and external layer(s) consisting of hydrophobic nano-particles.

In some embodiments, the composition comprises:
(i) hydrophobic nano-particles in an amount of 3-14% (by weight);
(ii) hydrophilic nano-particles in an amount of 1-3.5% (by weight);
(iii) amphiphilic particles in an amount of 2-4% (by weight);
and oil, wherein the ratio hydrophilic/hydrophobic mass should be in the range of 1:3 to 1:6 (by weight).

In some embodiments, the composition comprises (i) air bubbles bounded by internal layer(s) consisting of hydrophobic nano-particles and external layer(s) consisting of hydrophilic nano-particles, and (ii) water (or aqueous suspension) droplets bounded by internal layer(s) consisting of hydrophilic nano-particles and external layer(s) consisting of hydrophobic nano-particles.

In some embodiments, the composition further comprises skin-care ingredients for skin treatment.

In some embodiments, the composition is simultaneously an osmotic di-tonic relative to the treated skin.

In some embodiments, the hydrophilic metal oxide is silica ($SiO_2$).

In some embodiments, the hydrophobic metal oxide is silica ($SiO_2$), which at least 90% of particles' surface was modified to display hydrophobic character.

In some embodiments, the amphiphilic nano-particles are silica particles, which 40-60% of particles' surface was modified to display hydrophobic character. In some embodiments, said aqueous suspension is further characterized by comprising water droplets, or aqueous solution droplets, which are bounded by an internal layer of hydrophilic nano-particles defined in (ii) and an external layer of hydrophobic nano-particles defined in (i).

In some embodiments, comprising an oil.

Embodiments of the present invention provide a composition comprising an aqueous suspension, which comprises:
(i) metal (including silicon) oxide nano-particles displaying hydrophobic character, having diameters in the range of 1-150 nm;
(ii) metal (including silicon) oxide nano-particles displaying hydrophilic character, having diameters in the range of 1-150 nm;
(iii) amphiphilic micro-particles having diameters in the range of 1-100 μm;
wherein said aqueous suspension is characterized by comprising air gas bubbles bounded by an internal layer of hydrophobic nano-particles defined in (i) and an external layer of hydrophilic nano-particles defined in (ii).

In an embodiment of present invention, said aqueous suspension is further characterized by comprising water droplets, or aqueous solution or suspension droplets, which are bounded by an internal layer of hydrophilic nano-particles defined in (ii) and an external layer of hydrophobic nano-particles defined in (i).

In a further embodiment, the composition of present invention comprises oil.

In yet a further embodiment, the composition of present invention comprises micro-amphiphilic particles having diameters in the range of 1-50 μm.

In yet a further embodiment, the composition of present invention is used for cosmetic applications.

DESCRIPTION OF THE INVENTION

The invention is herein described, by way of example only.

For brevity, some explicit combinations of various features are not explicitly illustrated and/or described. It is now disclosed that any combination of the method or device features disclosed herein can be combined in any manner—including any combination of features—and any combination of features can be included in any embodiment and/or omitted from any embodiments.

Definitions

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

When 'particles' have diameter in the range of X and Y (where X and Y are both positive and have the dimension of length—e.g. microns or nanometers) this means that a mean diameter is in the range of X and Y. In some embodiments, this also means that at least 50% or at least 60% or at least 70% or a least 80% or at least 90% or at least 95% of the particles have an individual-particle diameter in the range of X and Y.

The skilled artisan will appreciate that some objects in the composition (e.g. particles or bubbles) may form aggregates or clusters—the diameter refers to the constitutive elements—i.e. individual nano or micro-particles and not to the diameter of the cluster as a whole.

The term 'internal' and 'external' are discussed in PCT/IL2002/000891 (incorporated herein by reference in its entirety)—the meaning in the present application is the same.

When a cylindrical container of an aqueous 'quick-drying composition' of dimensions 50 [ml] in volume and 13 cm^2 surface area (the entire container is enclosed and only open at its upper surface, circular in shape and having an area of 13 cm^2) is left open in a room having a constant temperature of 20 degrees Celsius and a relative humidity of 40%, the composition dries so that at least of the one 5% or at least 10% or at least 20% of the water of the composition leaves the composition (e.g. by evaporation) within a period of 24 hours.

In addition, the 'quick-drying composition' in said container under said conditions has its visible upper layer dry up and form cracks within 24 hours.

"Silicon" is included within the scope of the term "metal" when referred to as "metal-oxide."

"Water" includes water or any aqueous suspension.

"Air" includes any gaseous combination (including but not limited to nitrogen, oxygen, or any combination thereof, also with other gases).

The composition of present invention comprises a new particular combination of:
water or aqueous solution;
gas;
metal oxide nano-particles displaying hydrophobic character;
metal nano-particles displaying hydrophilic character; and
amphiphilic micro-particles, having diameters in the range of 1-100 μm.

More particularly, the present invention deals with the addition of micro-amphiphilic particles to the following Basic compositions which comprise metal oxide nano-particles displaying hydrophobic character (referred herein to as "hydrophobic metal oxide nano-particles" or simply "hydrophobic nano-particles") and metal oxide nano-particles displaying hydrophilic character (referred herein to as "hydrophilic metal oxide nano-particles" or simply "hydrophilic nano-particles"):

(i) Basic composition (I): is characterized by having bounded air bubbles and it comprises water, air, hydrophobic and hydrophilic nano-particles. The air bubbles are bounded by an internal layer made of hydrophobic nano-particles and an external layer made of hydrophilic nano-particles.

Such composition comprises the following amounts of the essential ingredients:

The amount of hydrophobic nano-particles is in the range of 1-3.5% (by weight) and the amount of hydrophilic nano-particles is in the range of 3-14% (by weight).

In order to avoid the creation of bounded water (or aqueous solution) droplets the hydrophobic nano-particles should not increase the amount of 3.5% (by weight) and the ratio hydrophilic/hydrophobic mass should be in the range of 3:1 to 6:1.

(ii) Basic composition (II): is characterized by having bounded water (or aqueous solution) droplets and it comprises water, air, hydrophobic and hydrophilic nano-particles, as well as oil. The water (or aqueous solution) droplets are bounded by an internal layer made of hydrophilic nano-particles and an external layer made of the hydrophobic nano-particles.

Such composition comprises the following amounts of the essential ingredients:

The amount of hydrophobic nano-particles is in the range of 3-14% (by weight) and the amount of hydrophilic nano-particles is in the range of 1-3.5% (by weight).

In order to avoid the creation of bounded air bubbles on one side and the formation of a regular dry powder (to distinguish from "watery-powder" which is a powder comprising bounded water droplets) on the other side the amount of hydrophobic nano-particles should not increase the amount of 14% (by weight) and the ratio hydrophilic/hydrophobic mass should be in the range 1:3 to 1:6 (by weight).

(iii) Basic composition (III): is a mixture of Basic compositions (I) and (II) and is characterized by having: (a) bounded air bubbles; and (b) bounded water (or aqueous solution) droplets.

It should be mentioned that the Basic compositions (I)-(III) are described by the inventors of present invention in the publications that were discussed in the chapter BACKGROUND OF THE INVENTION hereinbefore.

As was mentioned above, the present invention deals in finding a solution for overcoming the defects found in using the above Basic compositions. More particularly, the present invention deals with the addition of micro-amphiphilic particles to the above Basic compositions (I)-(III) for producing the following highly improved new and inventive compositions:

Composition B1 is formed by adding micro-amphiphilic particles to the Basic composition (I) and is characterized by having bounded air bubbles and it comprises hydrophobic and hydrophilic nano-particles, as well as amphiphilic micro-particles of diameters in the range of 1-100 μm. The air bubbles are bounded by an internal layer made of hydrophobic nano-particles and an external layer made of hydrophilic nano-particles.

Such composition comprises the following amounts of the essential ingredients:

The amount of hydrophobic nano-particles is in the range of 1-3.5% (by weight) and the amount of hydrophilic nano-particles is in the range of 3-14% (by weight).

In order to avoid the creation of bounded water (or aqueous solution) droplets the hydrophobic nano-particles should not increase the amount of 3.5% (by weight) and the ratio hydrophilic/hydrophobic mass should be in the range of 3:1 to 6:1 (by weight).

The formed bounded air bubbles in the suspension are mainly attracted to the hydrophilic groups on the surface of the amphiphilic micro-particles.

The amount of amphiphilic micro-particles in the suspension should be in the range of 2-4% (by weight).

The optional addition of oil will convert this suspension into an emulsion form.

It is speculated that the bounded air bubbles are mainly attracted to the hydrophilic zones on the amphiphilic micro-particles to produce a kind of clustered formation.

Composition B2 is formed by adding micro-amphiphilic particles to the Basic composition (II) and is characterized by having bounded water (or aqueous solution) droplets and it comprises hydrophobic and hydrophilic nano-particles, as well as amphiphilic micro-particles of diameters in the range of 1-100 μm and oil. The water (or aqueous solution) droplets are bounded by an internal layer made of hydrophilic nano-particles and an external layer made of hydrophobic nano-particles.

Such composition comprises the following amounts of the essential ingredients:

The amount of hydrophobic nano-particles is in the range of 3-14% (by weight) and the amount of hydrophilic nano-particles is in the range of 1-3.5% (by weight).

In order to avoid the creation of bounded air bubbles on one side and formation of regular dry powder (to distinguish from "watery-powder" which is a powder comprising bounded water droplets) on other side the amount of hydrophobic nano-particles should not increase the amount of 14% (by weight) and the ratio hydrophilic/hydrophobic mass should be in the range 1:3 to 1:6 (by weight).

The formed bounded water (or aqueous solution) droplets are mainly attracted to the hydrophobic groups on the surface of the amphiphilic micro-particles.

The amount of amphiphilic micro-particles in the suspension should be in the range of 2-4% (by weight).

It is speculated that the bounded water (or aqueous solution) droplets are mainly attracted to the hydrophobic zones on the amphiphilic micro-particles to produce a kind of clustered formation.

Composition B3 is formed by adding micro-amphiphilic particles to the Basic composition (III) and is characterized by having: (a) the bounded air bubbles; and (b) bounded water (or aqueous solution) droplets.

The amount of amphiphilic micro-particles should be in the range of 2-4% (by weight).

It should be mentioned that the amounts of amphiphilic particles in the above defined compositions of the invention, relate to an average amphiphilic particle which comprises a total of 40-60% (preferably, about 50%) hydrophobic zones and 60-40% (preferably, about 50%) hydrophilic zones on the particle's surface. In any case, the amount of amphiphilic particles should not disturb the balance (in mass terms) of the defined amounts of hydrophobic and hydrophilic nano-particles.

As described above, the following combinations as presented by the above Compositions B1 to B3 are within the scope of present invention:

| Case | Presence of bounded air bubbles | Presence of bounded water droplets | Presence of Amphiphilic Microparticles | Composition |
|---|---|---|---|---|
| 1 | Yes | No | Yes | B1 |
| 2 | No | Yes | Yes | B2 |
| 3 | Yes | Yes | Yes | B3 |

Generally speaking, increasing the mass of hydrophilic nano-particles in relation to hydrophobic nano-particles directs to the formation of bounded air bubbles, whereas increasing the mass of hydrophobic nano-particles in relation to the mass of hydrophilic nano-particles directs to the formation of bounded water (or aqueous solution) droplets.

In this respect, it should be pointed out that amphiphilic micro-particles do not take part in bounding air bubbles or water droplets. Thus, bounding air bubbles and water droplets, in the presence of amphiphilic micro-particles (having 1-100 μm diameters) is solely performed by hydrophobic and hydrophilic nano-particles. In such compositions the amphiphilic micro-particles play a major role in creating a clustered formation in which the bounded air bubbles and bounded water (or aqueous solution) droplets are attracted to the respective hydrophilic and hydrophobic zones on the surface of the amphiphilic micro-particles.

The above described compositions of present inventions (B1 to B3) display an improved stability and elasticity in temperatures higher than 40° C. In addition, the time required for skin treatment is reduced by 5-10 folds. In spite of such acceleration in time of skin treatment, the composition of present invention provides an improved amelioration process of skin disorders and skin appearance.

The composition of present invention comprises an aqueous suspension, which comprises at least the following components and ingredients:
water;
air;
hydrophobic metal oxide nano-particles having a diameter in the range of 1-150 nm;
hydrophilic metal oxide nano-particles having a diameter in the range of 1-150 nm;
amphiphilic particles, having diameters in the range of 1-100 μm;

In some cases addition of oil is optional (cf. Composition B1), while in others oil is served as an essential structural element (cf. Compositions B2 and B3). For forming an emulsion of Composition, B1 oil is optionally added after inserting the water.

In this specification, the term hydrophobic (or "modified hydrophobic") metal oxide nano-particles directs to hydrophilic metal oxide nano-particles, which are modified to display hydrophobic character.

The amphiphilic micro-particles used in the composition of present invention having diameters in the range of 1-100 μm, preferably 1 to 50 μm and most preferably, 1 to 30 μm.

There is a wide range of hydrophilic metal oxide nano-particles suitable for preparing the composition of present invention. The preferred hydrophilic metal oxide nano-particles are selected from the group consisting of silica ($SiO_2$), $Al_2O_3$, $TiO_2$, $Fe_2O_3$, MnO, ZnO, $CeO_2$ and combination thereof. Among these materials hydrophilic silica nano-particles are mostly preferred.

Similarly, there is a wide range of modified hydrophobic metal oxide nano-particles suitable for preparing the composition of present invention. The preferable modified hydrophobic metal oxide nano-particles are selected from the group consisting of silica ($SiO_2$), $Al_2O_3$, $TiO_2$, $Fe_2O_3$, MnO, ZnO, $CeO_2$ and combination thereof, which were chemically modified to display hydrophobic character. The mostly preferred hydrophobic nano-particles are hydrophobic silica nano-particles containing the group —Si(OR)n or —Si(R)n on their surface, wherein n represents 1, 2 or 3 and R represents a similar or different $C_1$ to $C_6$ alkyl group. Hydrophobic silica nano-particles in which R represents —$CH_3$ are the most preferable ones.

Preparing amphiphilic micro-particles are well known procedures in the literature (one example is U.S. Ser. No. 09/700,496). An amphiphilic particle is provided with hydrophobic and hydrophilic zones on its surface. Such hydrophobic-hydrophilic combined particle can bind liquids of opposite nature, for example, oil and water, creating a stable thixotropic water-oil emulsion. After the surprising discovery of the counter-intuitive benefits attained by Orgasol Caresse, additional tests are planned using other amphiphilic micro-particles with similar results. In one embodiment, amphiphilic particles can be prepared from commercial micronized hydrophobic silica particles, such as Sipernat D10, D13 and D17 by Evonik Industries AG, and Zeoflo TL by Huber Engineered Materials, using a temperature-controlled and time-controlled heating process, which removes some of the hydrophobic groups. The higher the time or temperature, the less phobic and more philic the particles become. In our experiments, temperatures in the range of 500 to 700 degrees Celsius were used, for 5 to 60 minutes, to achieve different hydrophobicity levels as measured by a methanol wettability test (% methanol in water required to reach 50% sediment under centrifugation).

Through the selection of particle size, surface area and hydrophobicity level, the properties of herein described cosmetic compositions can be optimized, for example to achieve less drying when packaged in a jar. One experimental method to choose such particle is by preparing a test set of compositions based on Example 1, which vary by:

% wt of entire composition of amphiphilic micro-particles (e.g. 2%, 3%, 4%)

Initial amphiphilic micro-particle (e.g. D10, D13, D17, Zeoflo TL, Orgasol)

Methanol wettability level (e.g. 10%, 15%, 20%, 25%, 30%—where applicable)

A control with no amphiphilic particles would be included in the test set.

Two groups of 50 ml cosmetic jars, each with every composition from the test set, would be filled with 50 ml and weighed right after filling with a precision of 0.1 gr. First group of jars would be closed and retained in a 40 degrees Celsius oven at 40% humidity. Every day each jar would be opened for 1 minute, weighed, and re-closed. Second group would be left open throughout the experiment, and similarly weighed. A 60 day observation should be sufficient to rank the each composition in terms of shelf-life stability.

The composition of embodiments of the present invention is characterized by the following parameters:

(i) The bounded air bubbles and bounded water (or aqueous solution) droplets may have characteristic diameters in the range of 1 μm to 50 μm.

(ii) The presence of amphiphilic micro-particles in the composition together with the bounded air bubbles and/or water droplets of a size in the range of tens of microns represents a format which corresponds to the skin structure where phobic/philic zones have these characteristic sizes (sebum and sweat outlets).

(iii) The concentration (by weight) of the hydrophobic nano-particles in the composition of present invention is such that the composition does not tend to become a regular dry powder, even in the presence of bounded water (or aqueous solution) droplets. Thus, the presence of amphiphilic micro-particles in the composition of present does not affect the total amount of hydrophobic metal oxide nano-particles that should not exceed 14% (by weight).

Further, the hydrophobic metal oxide nano-particles in the composition of present invention should have a characteristic specific surface greater than about 100 m$^2$/g. The same is true for the hydrophilic metal oxide nano-particles.

In addition to the ingredients described above, the composition of present invention may comprise one or more specific skin-care substances either in the form of a solute in aqueous solution and/or as suspended in oil.

Such skin-care ingredients may be selected, for example, from vitamins, essential oils, flavonoids, pigments, hyaluronic acid, bio-addition active materials, such as Hydriame® or other conventional skin-care ingredients.

It seems that a substantial part of the hydrophilic metal oxide nano-particles play a role in increasing the viscosity of the aqueous suspension, resulted in formation of a hydrophilic network in a gel-like structure, which comprises filaments of hydrophilic particles to which water molecules adhere.

The composition of present invention is preferably in a cream-like form. However, it may also be in the form of lotion, paste, ointment, gel and foam.

Generally speaking, the composition of present invention reduces skin wrinkles by means of forming a network of filaments upon applying to the skin. Such network functions to mechanically "pull out" wrinkle furrows in the skin, thereby smoothing the skin and drawing the skin taut.

More particularly, the cosmetic composition of present invention which consists of a combination of amphiphilic micro-particles, hydrophilic metal oxide nano-particles and hydrophobic metal oxide nano-particles in water and in the presence of air capable of forming on the skin a network of filaments following applying to the skin. The network anchors itself to the skin and to furrows of wrinkles in the skin. As a result of attraction between components of the cosmetic composition from which the filaments are formed, the filaments tend to contract with substantial force. Consequently, the network as a whole tends to contract. Since the filaments of the network are anchored to the skin and furrows of wrinkles therein, the network functions to mechanically "pull out" wrinkle furrows in the skin, thereby smoothing the skin and drawing the skin taut.

Thus, when the cosmetic composition of present invention is applied onto a region of skin, it forms a layer of cosmetic composition on the surface of the skin. Water from the attached cosmetic composition diffuse by osmoses into interstitial fluid and cells in the skin. As water leaves the attached cosmetic composition, the volume of the filaments produced by the hydrophilic metal oxide nano-particles contracts and the layer shrinks to a dried network of filaments on the skin. Each of the filaments is formed from a slurry of hydrophilic and hydrophobic particles in water. The hydrophilic and hydrophobic tendrils anchor the filaments to the skin region and wrinkle furrows therein.

In this respect, it is speculated that the presence of amphiphilic micro-particles contributes to the stabilization of the slurry and to the enhancement of interconnection between the hydrophobic and hydrophilic nano-particles, which results in facilitating the contraction.

Another speculated role of the amphiphilic micro-particles is that when they are in a rounded ball structure they are able to roll on the skin massaging and straightening it, like balls in bearings As a result of the attraction of the hydrophilic particles to water and less attraction of the hydrophobic particles to the hydrophilic particles and to water, the filaments tend to contract aggressively. Thus, the cosmetic filamentary network therefore tends to contract aggressively and thereby pulls out furrows of wrinkles in the skin and smoothes the skin.

The composition of present invention further provides a peeling effect that detaches dead skin cells from the surface of the epidermis. When the cosmetic composition is removed from the skin, the detached dead skin cells are removed with the composition's material. This is achieved, as a result of capillary action and attraction of hydrophilic and hydrophobic nano-particles in the cosmetic composition to moisture and natural oils in the skin respectively.

Water and hydrophilic and or hydrophobic nano-particles in the composition tend to penetrate between dead skin cells and the surface of the epidermis. If the skin is wet or moist, water and predominantly hydrophilic particles will tend to penetrate and concentrate between the dead skin cells and the epidermis. If the skin is oily, water and predominantly hydrophobic particles will tend to penetrate and concentrate between the dead skin cells and the epidermis. If the dead skin cells are dry, water in the cosmetic will tend to be absorbed by the dead skin cells resulting in their swelling. The penetration and concentration of the hydrophobic and/or hydrophilic particles between dead skin cells and the epidermis tends to pry up and dislodge the dead skin cells from the epidermis. Swelling of dry dead skin cells also tends to mechanically dislodge the dead skin cells from the epidermis. When the cosmetic substance is removed from the skin, the dislodged dead skin cells are removed with the cosmetic substance. It is speculated that amphiphilic micro-particles take part in mechanical rolling on the skin and absorption of dead dandruffs from it.

In addition to the applications mentioned above ("pull out" wrinkle furrows in the skin, thereby smoothing the skin and drawing the skin taut, and peel off dead skin cells from the epidermis), the composition of present invention [Composition B1 to B3] may be useful in topical treating a wide spectrum of skin disorders. In this respect, the composition of present invention may be formulated in several formations or versions—as follows:

(I) A Mono-Tonic (Isotonic or Hypotonic or Hypertonic) Composition

In the mono-tonic composition of present invention, the aqueous media and all the bounded water (or aqueous solution) droplets represent entities having the same osmotic tonicity (namely, isotonic or hypotonic or hypertonic) relatively to the skin. Thus, the hydrophilic and hydrophobic nano-particles in the aqueous suspension of present invention play role in bounding individual water (or aqueous solution) droplets having the same osmotic tonicity (isotonic or hypotonic or hypertonic) relatively to the skin.

In this respect, the following two major types of mono-tonic compositions should be considered:

(a) In the first type of mono-tonic composition of the invention, the aqueous suspension media and the separate, individual immiscible, stable bounded water (or aqueous solution) droplets are all hypotonic entities, relatively to the skin.

(b) In the second type of mono-tonic composition of the invention, the aqueous suspension media and the separate, individual immiscible, stable bounded water (or aqueous solution) droplets are all hypertonic entities, relatively to the skin.

These formats (a) and (b) of Compositions B2 and B3 provide two major types of functions:

(i) A composition comprising only hypotonic entities which direct the free and bounded aqueous content to flow towards and inward the skin, resulted in skin hydration effect; and (ii) A composition comprising only hypertonic entities which pump the water outward of skin, resulted in a skin dehydration effect.

(II) A Multi-Tonic (Isotonic and/or Hypotonic and/or Hypertonic) Composition

In the osmotic multi-tonic composition of present invention, the aqueous media and the bounded water (or aqueous solution) droplets each may represent an individual entity having particular osmotic tonicity, relatively to the skin (namely, isotonic, hypotonic, hypertonic) irrespective of other entities in the composition. Thus, the hydrophilic and hydrophobic nano-particles in the aqueous suspension of present invention play role in bounding water (or aqueous solution) droplets, wherein the aqueous suspension media and each of the individual bounded water droplets may represent an entity of different osmotic tonicity (isotonic, hypotonic or hypertonic), relatively to the skin, irrespective of other tonic entities.

The osmotic multi-tonic composition of the invention, which simultaneously comprises separate, individual immiscible, stable bounded hypotonic and hypertonic entities, relatively to the skin, represents a two-tonic format of compositions. Such two-tonic compositions may be represented by the following versions:

(i) The aqueous suspension is hypotonic, relatively to the skin, whereas all the individual bounded water (or aqueous solution) droplets are hypertonic, and vice versa;

(ii) The aqueous suspension is hypotonic, relatively to the skin, whereas part of the individual bounded water (or aqueous solution) droplets is hypotonic and the other part is hypertonic;

(iii) The aqueous suspension is hypertonic, relatively to the skin, whereas part of the individual bounded water (or aqueous solution) droplets is hypertonic and the other part is hypotonic.

Applying said two-tonic composition onto the skin resulted in gradually opening the bounded hypertonic and hypotonic entities, followed by multidirectional movement of ions from multiple, individual hypertonic entities into the skin, yielding a heterogeneous electrical field in the treated skin area with a substantial higher potential gradient, side by side with multidirectional flow of fluid, containing water and optionally skin-care ingredients, from the multiple, individual hypotonic entities towards the skin. This unique situation makes the composition of present invention useful and highly effective in a wide range of skin-care treatments and aesthetics.

The two-tonic variation of Compositions B2 and B3, which simultaneously comprises a mixture of plural microscopic, separate, immiscible, stable bounded hypertonic and hypotonic entities, relatively to the skin, was specifically designed for ameliorating and improving skin appearance during most prominent skin disorders that adversely affect skin, among them are eczematous dermatitis, papulosquamous disorders, viral and bacterial infections, carcinomous disorders and dermo-cosmetic disorders such as cellulite and hyperpigmentation. In addition, it is useful and highly effective in anti-aging, rejuvenation cosmetic treatments, such as wrinkles reduction, evening, as well as in whitening and/or lightening of skin complexion, and in protecting skin against UV radiation.

The simultaneous presence of plurality of individual immiscible, separate bounded hypertonic and hypotonic entities, relatively to variable skin constituents, makes the compositions of present invention an outstanding tool in ameliorating skin surface appearance. More specifically, applying such composition onto the skin provides a unique situation in which an electrical field, of heterogeneous plurality of multidirectional sites of high potential gradients is formed side by side with a multidirectional flow of liquid containing water and, optionally skin-care ingredients, inwardly, transversally and upwardly the skin. This unique situation is in contrast to conventional composition which unidirectional (inwardly) penetrates the skin and generally displays a rather limited effect on the potential gradient of local electric field.

In summary, the two-tonic variant of Compositions B2 and B3 in which separate hypotonic and hypertonic entities are simultaneously present in the composition seems to affect and ameliorate skin surface appearance by means of either of the following functions or activities:

(i) Forming a multidirectional flow of water or aqueous suspension inwardly, transversally and upwardly the skin. In this respect, it was surprisingly found that multidirectional flow of water (or aqueous solution) within the skin plays an important role in ameliorating skin surface appearance in cellulite, dermatitis and eczema.

(ii) Creating an electrical field of heterogeneous plurality of multidirectional sites of high potential gradients, within the skin, which surprisingly found as playing an important role in ameliorating skin surface appearance in psoriasis. It further reduces pain and pruritus.

(iii) Providing water-soluble skin-care ingredients that are released from multiple, individual bounded hypotonic entities. Such ingredients may be effective in whitening and/or lightening skin surface, in wrinkle reduction and in protection of skin against UV radiation.

(iv) Facilitating the skin penetration rate of water-non-miscible materials, contained in the composition of present invention, such as, for example, oil.

EXAMPLES

Example 1

Addition of Orgasol® (amphiphilic micro-particles produced by Arkema) to the basic composition (Leorex Booster Base) which comprises bounded air bubbles, hydrophobic and hydrophilic nano-particles. The Leorex Booster Base composition is highly useful in treating skin disorders, such as reducing skin wrinkles, and it comprises the following ingredients:

| Ingredient or component | wt % |
| --- | --- |
| Purified water USP | 81.33 |
| Hydrophilic silica (Aerosil 380) | 12.25 |
| Hydrophobic silica (Aerosil R812) | 2.5 |
| Propylene glycol | 3.0 |
| Glycacil ® 2000 (IPBC 6%) | 0.24 |
| Aloe vera powder | 0.23 |
| Methylparaben NF | 0.23 |
| Tocopheryl acetate | 0.11 |
| Vitamin A palmitate | 0.11 |
| Total: | 100.00 |

(a) Process for Preparing the Leorex Booster Base (Basic Composition):

5.58 g Methylparaben NF are added to 1950.67 g heated (75±2° C.) and rotated (55 rpm, rotations per minutes) purified water (USP) until methylparaben NF is totally solved. The rotated formed mixture (55 rpm) is cooled to 40±2° C.

5.58 g Aloe vera powder in 50 g purified water are added to the rotated (55 rpm) mixture at room temperature.

36.9 g Propylene glycol (USP) and 61.5 g Aerosil R812 (a commercial product of hydrophobic silica particles, having diameters in the range of 5-150 nm, produced by Degussa, Germany) are successively added to the rotated mixture at 30° C. until a homogenous mixture is formed. 100 g Aerosil 380 (a commercial product of hydrophilic silica nano-particles, having diameters in the range of 5-150 nm, produced by Degussa, Germany) and 5.9 g Glycacil® 2000 (IPBC 6%) are successively added to the rotated mixture (55 rpm). 100 g Aerosil 380 and 36.9 g propylene glycol (USP) are successively added to the rotated mixture (55 rpm). 101.35 g Aerosil 380 are added to the rotated mixture until a homogenous cream is formed. 2.8 g of tocopheryl acetate and of vitamin A palmitate are added to the rotated cream (55 rpm) and the mixed is further rotated until the structure of homogenous cream is restored. This cream is referred to as "Booster Base cream".

(b) Process for Preparing the New Leorex Booster Base:

75 g of Orgasol® (average particle size: 10 μm) dispersed in 615 g water are added to the formed cream mixture (the Booster Base cream) to form a new Leorex Booster Base composition, which comprises bounded air bubbles, hydrophilic and hydrophobic silica nano-particles and Orgasol® (amphiphilic micro-particles).

Example 2

Addition of Orgasol® and borage oil to the Leorex Booster Base. More particularly, 75 g of Orgasol® dispersed in 370 g water and 245 g borage oil are added to Leorex Booster Base of Example 1 to form a new Leorex Booster Base composition, which comprises bounded air bubbles, hydrophilic and hydrophobic silica nano-particles and Orgasol® (amphiphilic micro-particles).

Example 3

This example relates to the addition of Orgasol® to the basic composition which comprises bounded air, bounded water (or aqueous solution) droplets, hydrophobic and hydrophilic nano-particles. Such basic composition is highly effective in treating acne, psoriasis and atopic dermatitis.

(a) The Process for Preparing the Basic Watery-Powder Composition (Named "Capsules"):

| Ingredient or component | wt % |
| --- | --- |
| Hydrophilic silica nano-particles AE380 | 3.60 |
| Hydrophobic silica nano-particles R812 | 10.80 |
| Propylene glycol | 1.0 |
| Iodopropynyl butylcarbamate | 0.24 |
| Purified distilled water (Aqua) | 84.36 |
| Total: | 100.00 |

84 ml of purified distilled water are heated to a temperature of 75° C. 0.24 g of iodopropynyl butylcarbamate are added to the heated water following mixing until complete dissolution is obtained. 3.6 g of Aerosil 380 (AE380) are added while mixed for about 10 minutes in a mixer having a propeller rotating at about 1000 rpm. 1 g of propylene glycol are added using a mixer rotating in a speed of 2500-3000 rpm for about 10 minutes. 10.8 g of Aerosil R812 are added, following mixing for about 25-30 minutes at about 2500-3000 rpm. A watery-powder, which comprises bounded water (or aqueous suspension) droplets is obtained and it should be distinguished from the regular dry powder which does not contain bounded water droplets. This obtained watery-powder is referred to as "capsules".

(b) Mixing the "Capsules" with Leorex Booster Base Obtained in Example 1

In order to form a composition which comprises both bounded air bubbles and bounded water (or aqueous solution) droplets the "capsules" of this example are mixed with the Leorex Booster Base of Example 1. The formed 100 g composition (referred herein to as "basic bounded air bubbles and water droplets composition") should comprise 10% (by weight) of "capsules" and 90% (by weight) of Leorex Booster Base.

(c) Process for Adding Amphiphilic Micro-Particles to the Basic Bounded Air Bubbles and Water Droplets Composition.

3 gr Orgasol® dispersed in 15 g water and 10 g borage oil are added to 100 g of the formed basic bounded air bubbles and water droplets composition to form a new composition, which comprises bounded air bubbles, bounded water (or aqueous solution) droplets, hydrophilic and hydrophobic silica nano-particles and Orgasol® (amphiphilic micro-particles).

Example 4

The product of this example relates to a new mono-tonic composition (isotonic or hypotonic or hypertonic) relative to the treated skin. The composition which is highly effective in treating acne, eczema and atopic dermatitis comprises bounded air bubbles, hydrophobic nano-particles, hydrophilic nano-particles and amphiphilic micro-particles.

More particularly, this composition comprises Dead Sea salt in concentration (1 to 20 wt %) that provides the desired osmotic pressure. It may optionally contain 25-400 ppm of Ag and skin-care conventional ingredients.

The concentration of the salt in the composition is further determined according to the treated skin type (dried, oily, etc). Compositions containing higher concentrations of salt (such as, 10-20 wt %) are preferred for treating an oily skin.

(a) The Process for Preparing the Basic Composition ("Formed Cream Mixture")

875 g saline solution formed by dissolving 1 to 20 wt % Dead Sea salt (a commercial product which comprises $MgCl_2$ 33%, KCl 25%, NaCl 5.7%, $CaCl_2$ 0.3% and water 36%) in purified water (optionally containing Ag in an amount of 25-400 ppm) and 50 g Aerosil 380 (hydrophilic silica nano-particles), are mixed together for about 10 minutes in a mixer having a propeller rotating at about 1000 rpm. To the formed gel-like mixture, 25 g Aerosil R812 (hydrophobic silica nano-particles) are added successively in three batches: each batch which contains about 8.3 g is mixed for about 20 minutes at about 1000 rpm. Following the addition of Aerosil R812, the mixture is further mixed for about 30 minutes at 1500-1800 rpm. To the formed mixture, 50 g Aerosil 380 are added and the mixture is mixed for about 30 minutes at 1000 rpm. The formed mixture is set aside for a period of about 24 hours, during which it is maintained at a constant temperature of about 20° C. and isolated from mechanical vibration and shock. Following this "maturation" period, the formed mixture is ready for optionally insertion (generally, by mixing for 10 minutes at about 500 rpm) of one or more conventional skin-care ingredients, such as, for example, evening primrose oil (EPO), sweet almond oil, sea buckthorn oil, tea tree oil, borage oil, Finsolv TN ($C_{12}$-$C_{15}$ alkyl benzoate), octyl hydroxystearate, mathylparben, retinyl palmitate, aloe vera, vitamin E acetate, salicylic acid, vitamin C, citric acid and benzoyl peroxide. The obtained cream composition (referred herein to as "formed cream mixture") may comprise for example the following ingredients (by wt %).

| Case I | |
|---|---|
| Hydrophilic silica | 10.0 |
| Hydrophobic silica | 2.5 |
| Zinc acetate | 5.0 |
| Methylparaben | 0.1 |
| Retinyl palmilate | 0.1 |
| Aloe vera | 0.1 |
| Vitamin E acetate | 0.1 |
| Primrose oil | 3.0 |
| Sea buckthorn oil | 3.0 |
| Borage oil | 3.6 |

-continued

| Case I | |
|---|---|
| Water (containing 1-20 wt % Dead Sea salt) | 72.5. |

| Case II | |
|---|---|
| Hydrophilic silica | 7.5 |
| Hydrophobic silica | 2.5 |
| Dead Sea salt | 20.0 |
| Propylene glycol | 3.0 |
| Retinyl palmilate | 0.10 |
| Methyl paraben | 0.20 |
| Propyl paraben | 0.10 |
| Aloe barbadensis (Aloe vera) leaf powder | 0.10 |
| Tocopheryl acetate (Vitamin E) | 0.10 |
| Salicylic acid | 0.5 to 2.0 |
| Purified water | 64.4 to 65.9 (depending on the amount of salicylic acid) |

Note:
Similar formulations for treating acne containing higher concentrations of salicylic acid (such as, for example, 3-12 wt %), or 5-10% of benzoyl peroxide, are within the scope of present invention, as well.

(b) Process for Adding Amphiphilic Micro-Particles to the Formed Cream Mixture.

3 gr Orgasol® dispersed in 25 g water are added to 100 g of the formed cream mixture which comprises bounded air bubbles to form a new composition, which comprises bounded air bubbles, hydrophilic and hydrophobic silica nano-particles and Orgasol® (amphiphilic micro-particles).

Example 5

The product of this example relates to a multi-tonic osmotic composition (hypotonic and hypertonic) relative to the skin. The composition comprises bounded air bubbles, bounded water (or aqueous suspension) droplets, hydrophobic nano-particles, hydrophilic nano-particles and amphiphilic micro-particles.

This multi-tonic osmotic composition is suitable for treating acne and/or other skin disorders, such as, for example enlarged pores and scars, psoriasis and atopic dermatitis. Said composition relates to a formulation in which the hypertonic phase consists of a plural of individual bounded aqueous solution droplets containing Dead Sea salt and the hypotonic phase consists of a plural of individual bounded water (or aqueous solution) droplets containing no such electrolyte and/or ions. Both bounded water and aqueous solution droplets comprising an internal layer of hydrophilic nano-particles and an external layer of hydrophobic nano-particles.

(a) The Process for Preparing the Basic Watery-Powder Composition

The presence of bounded water and aqueous solution droplets in the watery-powder formation, distinguishes it from the regular dry powder.

The basic watery-powder comprises the following ingredients:

| Ingredient or component | wt % |
|---|---|
| Dead Sea salt | 3.00 |
| Hydrophobic silica nano-particles R812 | 10.80 |
| Hydrophilic silica nano-particles AE380 | 3.24 |

-continued

| Ingredient or component | wt % |
|---|---|
| 6-O-Palmitoyl-L-ascorbic acid | 2.00 |
| Phenoxyethanol | 0.80 |
| DMSO | 1.50 |
| Grape seed oil | 30.35 |
| Jojoba oil | 30.35 |
| Propylene glycol | 0.15 |
| Methylparaben | 0.06 |
| Propylparaben | 0.03 |
| Imidazoidinyl urea | 0.06 |
| Purified distilled water (Aqua) | 27.38 |
| Total: | 100.00 |

For preparing said watery-powder composition, each of the hypotonic and hypertonic phases is prepared in separated steps—as follows:

Step 1: Preparing the Hypertonic Phase

A watery-powder containing the following ingredients is prepared:

| Ingredient or component | wt % |
|---|---|
| Dead Sea salt | 20.00 |
| Hydrophilic silica nano-particles AE380 | 3.60 |
| Hydrophobic silica nano-particles R812 | 10.80 |
| Methylparaben | 0.20 |
| Propylparaben | 0.10 |
| Imidazoidinyl urea | 0.20 |
| Purified distilled water (Aqua) | 65.10 |
| Total: | 100.00 |

250 ml of purified distilled water are heated to a temperature of 75° C. 0.78 g of methylparaben, 0.238 g of propylparaben and 0.78 g of imidazodinyl urea are added to the heated water following mixing until complete dissolution is obtained. 13.82 g of Aerosil 380 (or AE380) are added while mixed for about 10 minutes in a mixer having a propeller rotating at about 1000 rpm. 76.80 g of Dead Sea salt (comprising a mixture of MgCl$_2$ 33%, KCl 25%, NaCl 5.7% and CaCl$_2$ 0.3%) are added, using a mixer rotating in a speed of 700-800 rpm until a complete dissolution of the salt is obtained. 41.47 g of Aerosil R812 are added, following mixing for about 25-30 minutes at about 2500-3000 rpm. The obtained powder is referred to as "the hypertonic watery-powder".

Step 2: Preparing the Hypotonic Phase

A watery-powder containing the following ingredients is prepared:

| Ingredient or component | wt % |
|---|---|
| Hydrophilic silica nano-particles AE380 | 3.60 |
| Hydrophobic silica nano-particles R812 | 10.80 |
| Propylene glycol | 1.00 |
| Methylparaben | 0.20 |
| Propylparaben | 0.10 |
| Imidazoidinyl urea | 0.20 |
| Purified distilled water (Aqua) | 84.10 |
| Total: | 100.00 |

200 ml of purified distilled water are heated to a temperature of 75° C. 0.456 g of methylparaben, 0.238 g of propylparaben and 0.456 g of imidazodinyl urea are added to the heated water following mixing until complete dissolution is obtained. 8.56 g of Aerosil 380 or AE380 are added while mixed for about 10 minutes in a mixer having a propeller rotating at about 1000 rpm (rotations per minute). 2.37 g of propylene glycol are added using a mixer rotating in a speed of 2500-3000 rpm for about 10 minutes. 25.60 g of Aerosil R812 are added, following mixing for about 25-30 minutes at about 2500-3000 rpm. The obtained powder is referred to as "the hypotonic watery-powder".

Step 3: Mixing the Hypotonic and Hypertonic Phases Prepared in the Above Steps:

In this step the products of step 1 (the hypertonic watery-powder) and step 2 (the hypotonic watery-powder) are mixed with a mixture of various oil(s) and other skin-care ingredients to form the multi-tonic osmotic composition of present example:

100 g of jojoba oil are heated to a temperature of 40° C. The following ingredients are successively added to the heated jojoba oil, followed by mixing the formed mixture after insertion of each ingredient:

10.05 g of 6-O-palmitoyl-L-ascorbic acid 100 g of grape seed oil 5.02 g of DMSO (dimethyl sulfoxide)

50.25 g of the product of step 2 (the hypotonic watery-powder)

50.25 g of the product of step 1 (the hypertonic watery-powder)

2.68 g of phenoxyethanol

The formed mixture constitutes the basic watery-powder.

(b) Mixing the Basic Watery-Powder with Leorex Booster Base Obtained in Example 1

In order to form a composition which comprises both bounded air bubbles and bounded water (or aqueous solution) droplets the basic watery-powder of this example are mixed with the Leorex Booster Base of Example 1. The formed 100 g composition (referred herein to as "basic bounded air bubbles and water droplets composition") should comprise 10% (by weight) of basic watery-powder and 90% (by weight) of Leorex Booster Base. The obtained composition is in a cream form.

(c) Process for Adding Amphiphilic Micro-Particles to the Basic Bounded Air Bubbles and Water Droplets Composition.

3 gr Orgasol® dispersed in 15 g water and 10 g borage oil are added to 100 g of the formed basic bounded air bubbles and water droplets composition to form a new composition, which comprises bounded air bubbles, bounded water and aqueous solution droplets, hydrophilic silica nano-particles, hydrophobic silica nano-particles and Orgasol® (amphiphilic micro-particles).

GENERAL

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A topically administrable composition comprising:
   an aqueous suspension, said aqueous suspension having disposed therewithin amphiphilic micro-particles having diameters in the range of 1-100 μm, wherein hydrophobic and hydrophilic zones are each present on the surface of each of the amphiphilic micro-particles, wherein said aqueous suspension comprises:
   A. hydrophobic nanoparticles of modified metal oxide and/or modified silicon oxide having diameters in the range of 1-150 nm;
   B. hydrophilic nanoparticles of metal oxide and/or silicon oxide having diameters in the range of 1-150 nm; and
   C. gas bubbles which are bounded by an internal layer of said hydrophobic nanoparticles and an external layer of said hydrophilic nanoparticles.

2. The composition of claim 1 wherein the aqueous suspension is quick-drying.

3. The composition of claim 1 wherein the hydrophobic nanoparticles of modified metal oxide and/or modified silicon oxide have diameters in the range of 1-75 nm, or 1-50 nm, or 1-25 nm, or 1-15 nm, or 1-10 nm.

4. The composition of claim 1 wherein the hydrophilic nanoparticles of metal oxide and/or silicon oxide have diameters in the range of 1-75 nm, or 1-50 nm, or 1-25 nm, or 1-15 nm, or 1-10 nm.

5. The composition of claim 1 wherein the amphiphilic micro-particles have diameters in the range of 1-50 μm, or in the range of 1-25 μm, or in the range of 1-15 μm, or in the range of 1-10 μm.

6. The composition of claim 1 wherein: (i) the amphiphilic particles are present in the composition in an amount of a–b % by weight; (ii) a and b are both positive numbers; (iii) a value of a is at least 1 or at least 2 or at least 3 or at least 4 or at least 5 and/or a value of b is at most 20 or at most 15 or at most 10 or at most 8 or at most 6 or at most 5 or at most 4.

7. The composition of claim 1 wherein the amphiphilic micro-particles are spherical.

8. The composition of claim 1 wherein the amphiphilic micro-particles comprise a plastic and/or comprise a polyamine and/or comprise a copolyesteramide.

9. The composition of claim 1 wherein the amphiphilic micro-particles have a microporosity so that a per-particle surface area is between 1 and 100 meters$^2$/gram.

10. The composition of claim 1 wherein said hydrophobic modified metal oxide nano-particles are present in an amount of 1-3.5% by weight of said composition; said metal oxide nano-particles are present in an amount of 3-14% by weight of said composition; said amphiphilic particles are present in an amount of 2-4% by weight; of said composition; and
    the mass ratio of hydrophilic particles to hydrophobic particles is in the range of 3:1 to 6:1.

11. The composition of claim 1 wherein said
    hydrophobic modified nano-particles metal oxide and/or silicon oxide are present in said composition in an amount of 3-14% by weight;
    (ii) hydrophilic nano-particles of metal oxide and/or silicon oxide in an amount of 1-3.5% by weight;
    (iii) amphiphilic particles in an amount of 2-4% by weight;
    wherein the ratio hydrophilic/hydrophobic mass is in the range of 1:3 to 1:6 by weight.

12. The composition of claim 1, comprising at least one of mineral salts, vitamins, oils, flavonoids and pigments.

13. The composition of claim 1, in any one of the following forms: cream or cream-like, lotion, paste, ointment, gel and foam.

14. The composition of claim 1 being an osmotic monotonic relative to human skin.

15. The composition of claim 14, being hypotonic relative to human skin.

16. The composition of claim 14, being hypertonic relative to human skin.

17. The composition of claim 14, being isotonic relative to the treated skin.

18. The composition of claim 1 being simultaneously an osmotic multi-tonic relative to the treated skin.

19. The composition of claim 1 being simultaneously hypotonic and hypertonic relative to the treated skin.

20. Use of the composition of claim 1 for use in cosmetic applications.

21. The composition of claim 1 wherein, on average, (i) 40-60% of a surface of each of the amphiphilic micro-particles is occupied by the hydrophobic zones, and (ii) 40-60% of a surface of each of the amphiphilic micro-particles is occupied by the hydrophilic zones.

* * * * *